United States Patent [19]

Peyman et al.

[11] Patent Number: 6,026,815
[45] Date of Patent: Feb. 22, 2000

[54] RADIOPAQUE LIQUID AS RADIATION BLOCKING AGENT

[75] Inventors: Gholam A. Peyman, 8654 Pontchartrain Blvd., Apt 1, New Orleans, La. 70124; Webb Bailey, Roundrock, Tex.

[73] Assignee: Gholam A. Peyman, New Orleans, La.

[21] Appl. No.: 08/948,370

[22] Filed: Oct. 8, 1997

Related U.S. Application Data

[60] Provisional application No. 60/028,205, Oct. 10, 1996.

[51] Int. Cl.[7] ............................................. A61B 19/00
[52] U.S. Cl. .................................. 128/898; 623/4; 252/478
[58] Field of Search .............................. 128/898; 623/4, 623/5, 6; 252/478

[56] References Cited

U.S. PATENT DOCUMENTS

| | | | |
|---|---|---|---|
| 3,911,138 | 10/1975 | Clark, Jr. | 424/352 |
| 3,975,512 | 8/1976 | Long | 424/5 |
| 4,490,351 | 12/1984 | Clark, Jr. | 424/5 |
| 4,865,836 | 9/1989 | Long, Jr. | 424/5 |
| 5,514,720 | 5/1996 | Clark, Jr. et al. | 514/749 |
| 5,528,652 | 6/1996 | Smith et al. | 378/65 |
| 5,536,753 | 7/1996 | Clark, Jr. | 514/749 |
| 5,767,092 | 6/1998 | Koezuka et al. | 514/25 |

OTHER PUBLICATIONS

Murata et al., Perfluoroctylbromide emulsion, J. Jpn. Soc. Cancer Ther. 23(1): 104–113, 1988.

Carr et al., Microvascular studies in human radiation bowel disease, Gut., 1984, 25, 448–454.

Persliden et al., Comparison of absorbed radiation doses in barium and air enema reduction of intussusception: a phantom study, Pediatr Radiol (1996) 26:329–332, 1996.

Rockwell et al., Effects of Hyperbaric Oxygen and Perfluorooctylbromide emulsion on the radiation responses of tumors and normal tissues in rodents, I. J. Radiation Oncology Biol. Phys. vol. 22, pp. 87–93, 1991.

Char, D.H. et al., *Helium Ion Therapy for Choroidal Melanoma*, Arch Opthalmol 100:935–938, 1982.

Gragoudas, E.S. et al., *Proton Beam Irradiation of Uveal Melanomas: Results of 5 1/2–Year Study*, Arch Ophthalmol 100:928–934, 1980.

Shields, J.A. et al., *Cobalt Plaque Therapy of Posterior Uveal Melanomas*, Opthalmology 89:1201–1207,1982.

Packer, S. et al., *Radiotherapy of Choroidal Melanoma with Iodine–125*, Opthalmology 87:582–590,1980.

Kim, M.K. et al., *Neovascular Glaucoma After Helium–Ion Radiation for Uveal Melanoma*, Opthalmology 93:189–193, 1986.

*Primary Examiner*—Michael J. Milano
*Assistant Examiner*—Dinh X. Nguyen
*Attorney, Agent, or Firm*—Wood, Herron & Evans, L.L.P.

[57] ABSTRACT

A radiopaque liquid to protect normal tissue from radiation induced damage. A radiopaque liquid such as a fluorocarbon is introduced into a body cavity to protect tissues adjacent to a target radiation site. The radiopaque liquid prevents radiation penetration into protected cavities. In one embodiment, perfluorooctylbromide is used as the radiopaque liquid to replace vitreous gel in irradiating an intraocular tumor.

15 Claims, 1 Drawing Sheet

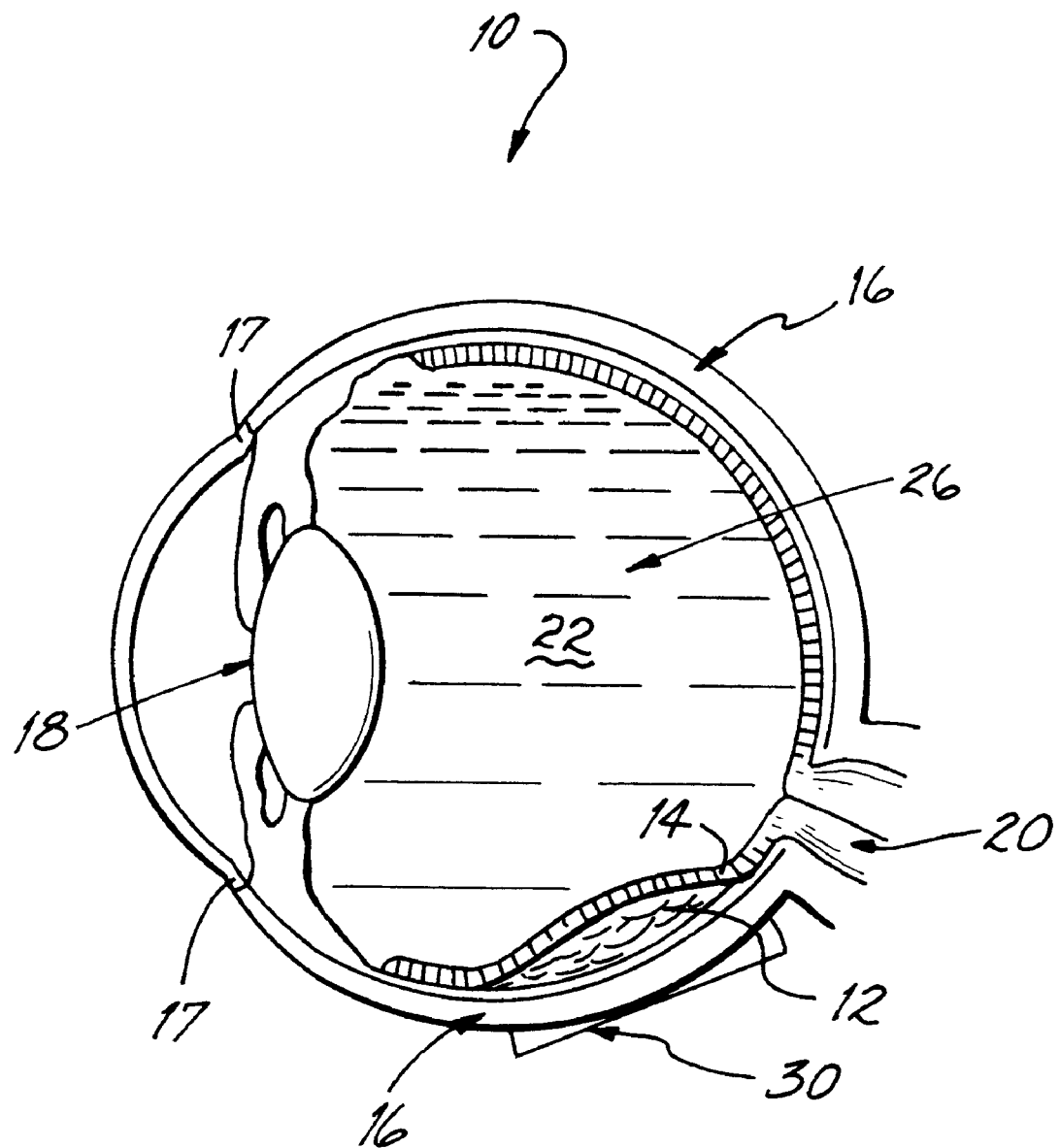

RADIOPAQUE LIQUID AS RADIATION BLOCKING AGENT

RELATED APPLICATION

This application claims the benefit of U.S. Provisional Application No. 60/028,205 filed Oct. 10, 1996.

BACKGROUND OF THE INVENTION

Radiotherapy has a long history in the treatment of malignant tumors of the body. Many malignant tumors are treated by radiotherapy, either alone or in some combination with surgical resection and/or systemic administration of antiproliferative agents. While radiation can successfully stop tumor growth, its side effects are well known. One serious side effect is scar formation adjacent to the site of radiation. Such scar formation often results in damage to or constriction of important structures located behind the target radiation site.

A similar situation exists with regard to intraocular tumors. The majority of adult malignant tumors of the eye are malignant melanoma. They are treated by enucleation if they are large, or by radiotherapy, or by surgical resection of the tumor.

In the eye, radiation damages not only the tissue surface, but often damages tissues that are adjacent to the target radiation site. These side effects produce cataract formation, radiation retinopathy, radiation optic nerve neuropathy, and vitreous hemorrhage. Radiation retinopathy manifests itself as a result of damage to the vascular supply of the retina and optic nerve. Neuropathy is induced by damage to the vascular supply of the optic nerve head or the optic nerve itself. The severity of the side effects often relate to the location of the tumor; for example, close to the fovea, the most sensitive structure of the retina, or close to the optic nerve head.

Two forms of radiation therapy are used to treat malignant tumors of the eye. One form is external beam radiation, where the source of radiation can be an x-ray or proton beam or helium ion radiation. The second form is the use of radioactive plaques or radioactive seeds which are sutured to the sclera behind the tumor.

In external beam radiation, the radiation passes through normal body structures before it reaches the target radiation site, which is the tumor. After reaching the tumor, it also penetrates tissues located adjacent to the tumor, such as tissues on the side of and behind the tumor. In radioactive plaque administration, such as with $^{125}$I or radioactive seeds, radiation is generally unidirectional and hence the beam scatter is minimized. The forward direction of the beam, however, will not limit itself to the tumor, but also penetrates normal structures of the eye. Therefore, in treating intraocular tumors structures such as the lens, retina, or optic nerve can also be damaged. A similar situation exists in other areas of the body, such as in the treatment of prostate cancer, lung tumors, or tumors located in the neck or base of the skull.

SUMMARY OF THE INVENTION

This invention is directed to a method of protecting normal tissues adjacent to a target radiation site from radiation-induced damage by shielding them with radiopaque liquids which prevent radiation penetration. The liquids can be administered as neat liquids, mixtures or emulsions and may include fluorocarbons or other radiocontrast media.

When the target radiation site is an intraocular tumor, unaffected tissues in the eye can be protected by removing the vitreous gel and replacing it with perfluorooctylbromide, a specific radiopaque fluorocarbon liquid. The perfluorooctylbromide will block the radiation and thus will reduce the damage to the normal structures of the eye located on the other side of the eye wall. The target radiation site, the tumor, can then be irradiated either by using a radioactive plaque or proton beam or helium ion radiation.

When the target radiation site is located in parts of the body other than the eye, perfluorooctylbromide, a mixture of perfluorooctylbromide with other fluorocarbon liquids, or other radiopaque liquids such as barium sulfate can be used to protect adjacent tissues from radiation-induced damage. The neat liquid or mixture can be injected in tissues adjacent to the radiation target site, such as soft tissues behind a tumor. Alternatively, it can be introduced into body cavities such as the bladder, ureter, esophagus, stomach (i.e., by gavage), lung, brain, abdomen, and intestine by catheter, a combination of catheter and balloon, or by other means such as a cocktail. The liquid in the form of an emulsion can also be injected intravenously prior to radiation therapy to protect important blood vessels from radiation-induced damage.

BRIEF DESCRIPTION OF THE DRAWING

The FIGURE is a cross-section of a mammalian eye treated by the method of the invention.

DETAILED DESCRIPTION OF THE INVENTION

With reference to the FIGURE, a mammalian eye 10 containing an intraocular tumor 12 is shown. The tumor 12 is located adjacent to the retina 1 4 and displaces the retina 14. The sclera 16, lens 18 and optic nerve 20 are also shown. The vitreous body 22 normally contains vitreous gel (not shown).

Perfluorooctylbromide 26, either alone or as part of a mixture of fluorocarbons, is used as a radiation blocking agent in the treatment of an intraocular tumor 12. The surgical technique involves performing a routine vitrectomy, three port, at the pars plana of the conjunctiva 17, followed by removal of the vitreous gel (not shown) with a vitrectomy instrument. The vitreous gel (not shown) is replaced with perfluorooctylbromide 26 or a mixture of perfluorooctylbromide 26 with other fluorocarbon liquids injected through a syringe.

As illustrated in the FIGURE, and according to the method of the invention, vitreous gel (not shown) is replaced by perfluorooctylbromide 26. After localization of the tumor 12, a radioactive plaque 30 is sutured from outside the eye 10 to the sclera 16 over the area of the tumor 12. The plaque 30 is left in place for a period of time, for example, five to ten days, to achieve the desired amount of radiation exposure. After this time, the conjunctiva 17 is again opened with the patient under a general or local anesthesia, and the radioactive plaque 30 is removed. The perfluorooctylbromide 26 or other fluorocarbon liquid is also removed at this time by evacuation from the vitreous body 22 using standard methods. For example, normal physiologic saline solution may be infused, or air or other gas may be added while removing the perfluorooctylbromide 26 or other fluorocarbon liquid from the vitreous body 22. The incision is closed at the end of the surgery and antibiotic ointment and drops are applied to the eye 10. The patient is then followed postoperatively using routine procedures.

Similarly, perfluorooctylbromide 26 or other fluorocarbon liquid can be injected behind the eye 10 or in the sinuses prior to radiation of the tumor 12 located in an adjacent area.

The fluorocarbon liquid can be removed from the cavities by aspiration or may remain there to be resorbed and exhaled through the lungs.

It should be understood that the embodiments of the present invention shown and described in the specification are only preferred embodiments of the inventors who are skilled in the art and are not limiting in any way. Therefore, various changes, modifications or alterations to these embodiments may be made or resorted to without departing from the spirit of the invention and the scope of the following claims.

What is claimed is:

1. A method of protecting normal mammalian tissues from radiotherapy damage, comprising the step of introducing prior to radiation a radiopaque fluorocarbon liquid comprising a radiopaque substance into said tissues located adjacent to a target radiation site thereby protecting said normal tissues from radiation penetration.

2. The method of claim 1 wherein said liquid is a neat liquid.

3. The method of claim 1 wherein said liquid is a mixture.

4. The method of claim 1 wherein said liquid is in the form of an emulsion.

5. The method of claim 1 wherein said liquid is introduced by injection.

6. The method of claim 1 wherein said fluorocarbon comprises a mixture of perfluorooctylbromide and other fluorocarbon liquids.

7. The method of claim 1 wherein said fluorocarbon is perfluorooctylbromide.

8. The method of claim 7 wherein said perfluorooctylbromide is introduced into the vitreous body of the eye substantially replacing vitreous gel.

9. The method of claim 1 wherein the normal mammalian tissues are adjacent to abnormal tissues to be treated with radiation and further comprising the step of irradiating the abnormal tissues.

10. The method of claim 9 wherein the abnormal tissues are a tumor.

11. A method of protecting normal mammalian organs from radiotherapy damage, comprising the step of introducing prior to radiation a radiopaque fluorocarbon into cavities of said organs, wherein said organs are selected from the group consisting of:

a bladder, a ureter, an esophagus, a stomach, a lung, a brain, an abdomen, an intestine, a blood vessel, and combinations thereof.

12. The method of claim 11 wherein said liquid is introduced by catheter.

13. The method of claim 11 wherein said liquid is introduced by a combination of catheter and balloon.

14. The method of claim 11 wherein said liquid is introduced by gavage.

15. The method of claim 11 wherein said liquid is introduced by administration as a cocktail.

* * * * *

UNITED STATES PATENT AND TRADEMARK OFFICE
CERTIFICATE OF CORRECTION

PATENT NO. : 6,026,815

DATED : February 22, 2000

INVENTOR(S) : Gholam A. Peyman, et al.

It is certified that error appears in the above-identified patent and that said Letters Patent is hereby corrected as shown below:

Column 3, line 16, delete "comprising a radiopaque substance".

Signed and Sealed this

Thirteenth Day of June, 2000

*Attest:*

Q. TODD DICKINSON

*Attesting Officer*  *Director of Patents and Trademarks*

UNITED STATES PATENT AND TRADEMARK OFFICE
CERTIFICATE OF CORRECTION

PATENT NO. : 6,026,815
DATED : February 22, 2000
INVENTOR(S) : Gholam A. Peyman, et al.

It is certified that error appears in the above-indentified patent and that said Letters Patent is hereby corrected as shown below:

Claim 1, line 4, "comprising a radiopaque substance"

delete:
"comprising a radiopaque substance"

Claim 11 (originally Claim 12), line 3, "fluorocarbon into"

should be:
--fluorocarbon liquid into--

Signed and Sealed this

Twenty-sixth Day of December, 2000

Attest:

Q. TODD DICKINSON

Attesting Officer

Director of Patents and Trademarks